(12) United States Patent
Marillia et al.

(10) Patent No.: US 7,214,859 B2
(45) Date of Patent: ***May 8, 2007

(54) BRASSICA PYRUVATE DEHYDROGENASE KINASE GENE

(75) Inventors: Elizabeth-France Marillia, Near Asquith (CA); Jitao Zou, Saskatoon (CA); David C. Taylor, Saskatoon (CA)

(73) Assignee: National Research Council of Canada, Ottawa (CA)

( * ) Notice: Subject to any disclaimer, the term of this patent is extended or adjusted under 35 U.S.C. 154(b) by 65 days.

This patent is subject to a terminal disclaimer.

(21) Appl. No.: 10/642,531

(22) Filed: Aug. 15, 2003

(65) Prior Publication Data

US 2004/0248302 A1    Dec. 9, 2004

Related U.S. Application Data

(63) Continuation-in-part of application No. 10/222,075, filed on Aug. 16, 2002, now Pat. No. 7,057,091.

(51) Int. Cl.
    C12N 15/29    (2006.01)
    C12N 15/82    (2006.01)

(52) U.S. Cl. .............. 800/298; 536/23.6; 800/278; 800/306

(58) Field of Classification Search .............. 536/23.1; 800/295; 435/320.1
    See application file for complete search history.

(56) References Cited

U.S. PATENT DOCUMENTS

| | | | |
|---|---|---|---|
| 5,102,796 A | 4/1992 | Hall et al. | |
| 5,504,200 A | 4/1996 | Hall et al. | |
| 5,510,474 A | 4/1996 | Quail et al. | |
| 5,591,605 A | 1/1997 | Hall et al. | |
| 5,614,399 A | 3/1997 | Quail et al. | |
| 6,054,574 A | 4/2000 | Quail et al. | |
| 6,265,636 B1 * | 7/2001 | Randall et al. ............. | 800/295 |
| 6,500,670 B1 * | 12/2002 | Zou et al. ................. | 800/295 |

FOREIGN PATENT DOCUMENTS

WO    WO 98/35044 A1    8/1998

OTHER PUBLICATIONS

U.S. Appl. No. 10/222,075, filed Aug. 2002, Zou et al.*
Kirill M. Popov et al., "Primary Structure of Pyruvate Dehydrogenase Kinase Establishes a New Family of Eukaryotic Protein Kinases." The Journal of Biological Chemistry, vol. 268, No. 35, Issue of Dec. 15, pp. 26602-26606, 1993.
Ramavedi Gudi et al., "Diversity of the Pyruvate Dehydrogenase Kinase Gene Family in Humans," The Journal of Biological Chemistry, vol. 270, No. 48, Issue of Dec. 1, pp. 28989-28994, 1995.

E. Ellen Reid et al., "Pyruvate Dehydrogenase Complex from Higher Plant Mitochondria and Proplastids," Plant Physiol. (1977) vol. 59, pp. 842-848.
Christopher, P.L. Grof. et al., "Mitochondrial Pyruvate Dehydrogenase," Plant Physiol. (1995) vol. 108, pp. 1623-1629.
Tom Newman et al., Genes Galore: A Summary of Methods for Accessing Results from Large-Scale Partial Sequencing of Anonymous Arabidopsis cDNA Clones, Plant Physiol. (1994) vol. 106, pp. 1241-1255.
2002 Life Technologies Product catalog 3' RACE System for Rapid Amplification of cDNA Ends, 21-25, 1 page.
2002 Life Technologies Product catalog, 5' RACE System for Rapid Amplification of cDNA Ends, Version 2.0, 21-22, 1 page.
2002 Life Technologies Product catalog, M-MLV Reverse Transcriptase, 16-25, 1 page.
Zou, Jitao et al., "Effects of antisense repression of an *Arabidopsis thaliana* pyruvate dehydrogenase kinase cDNA on plant development," National Research Council of Canada, Plant Biotechnology Institute, 110 Gymnasium Place, Saskatoon, Saskatchewan, Canada, S7N 0W9, Plant Molecular Biology 41:837-849, 1999, © 1999 Kluwer Academic Plublishers, Printed in the Netherlands.
Zou, Jitao et al., Cloning and characterization of an *Arabidopsis thaliana* mitochondrial pyruvate dehydrogenase kinase gene and effects of antisense repression on plant development and seed oil content. ABIC, Saskatoon, SK, Jun. 9-12, 1998.
Zou, J-T et al., Does Mitochondrially-Generated Acetate Contribute to Plastidial Fatty Acid Biosynthesis? Antisense repression of an *Arabidopsis thaliana* mitochondrial pyruvate dehydrogenase kinase (PDHK) gene and its effects on oil content and plant development, poster and abstract B71; 13th International Symposium on Plant Lipids, Sevilla, Spain, Jul. 5-10, 1998.
Thelen, Jay J. et al., "Pyruvate dehydrogenase kinase from *Arabidopsis thaliana*: a protein histidine kinase that phosphorylates serine residues," Biochem. J. (2000) 349, 195-201, (Printed in Great Britain).
Mooney, Brian P. et al., Biochemistry Department, University of Missouri, Columbia Missouri 65211; and Plant Genetics Research Unit, USDA, ARS, Columbia, Missouri, 65211, "Histidine Modifying Agents Abolish Pyruvate Dehydrogenase Kinase Activity," Biochemical and Biophysical Research Communications, 267, 500-503 (2000).
Thelen, Jay J. et al., "Molecular Analysis of Two Pyruvate Dehydrogenase Kinases from Maize," The Journal of Biological Chemistry, vol. 273, No. 41, Issue of Oct. 9, 1998, pp. 26618-26623.

(Continued)

*Primary Examiner*—David H Kruse
(74) *Attorney, Agent, or Firm*—TraskBritt

(57) ABSTRACT

The isolation, purification, characterization and use of a mitochondrial pyruvate dehydrogenase kinase (PDHK) gene from *Brassica* spp. Methods of regulating fatty acid synthesis, seed oil content, seed size/weight, flowering time, vegetative growth, respiration rate and generation time using the gene and to tissues and plants transformed with the gene. Transgenic plants, plant tissues and plant seeds having a genome containing an introduced *Brassica* DNA, characterized in that the sequence has been introduced in an antisense or sense orientation, and a method of producing such plants and plant seeds.

22 Claims, 6 Drawing Sheets

OTHER PUBLICATIONS

Marillia et al., Characterization of an *Arabidopsis thaliana* mitochondrial pyruvate dehydrogenase kinase gene and effects of antisense repression on plant development, Abstract and poster #24, pp. 99, Proceedings of the Canadian Society of Plant Physiologists Meeting, Plant Biology Canada '99, Saskatoon, SK, Jun. 19-23, 1999.

Marillia, et al., "Biochemical and physiological studies of *Arabidopsis thaliana* transgenic lines with repressed expression of the mitochondrial pyruvate dehydrogenase kinase," Journal of Experimental Botany, http://jxb.oupjournals.org/cgi/content/abstract/54/381/259, 2 pages (Aug. 14, 2003).

Marillia et al., "Metabolic engineering of Brassica seeds oils: improvement of oil quality and quantity and alteration of carbon flux." Plant Genetic Engineering: Towards the Third Millenium, 2000, pp. 182-188, Elsevier Science Publishing: New York.

GenBank Accession No.: AF038585, 1998.

GenBank Accession No.: AF038586, 1998.

* cited by examiner

```
                        SEQUENCE LISTING

<160> NUMBER OF SEQ ID NOS: 19

<210> SEQ ID NO 1
<211> LENGTH: 1104
<212> TYPE: DNA
<213> ORGANISM: Brassica napus
<220> FEATURE:
<223> OTHER INFORMATION: PDHK cDNA from B. napus

<400> SEQUENCE: 1
atggcggtga agaaggctag cgagatgttt tcgaagagct tgatcgagga cgttcacaga      60
tggggatgca tgaagcagac gggcgtgagc ctcaggtaca tgatggagtt cggttccact     120
cccactgaga gaaaccttct gatctcggcg cagtttcttc acaaggagct tccgattcgg     180
atcgcgaggc gtgcgatcga actcgagacg ctgccttatg gcctctctga gaaacctgcc     240
gtcttgaagg taagagattg gtatgtggag tcattcaggg acatgagagc gtttcctgag     300
atcaaggata ctgctgatga gaaagagttc acacagatga tcaaggctgt taaagtaagg     360
cacaacaacg tggttcccat gatggctctg ggtgtgaacc agctgaagaa aggaatgaaa     420
ctctacgaaa agcttgatga gattcatcag tttcttgatc gcttctactt gtctcgtata     480
gggatccgta tgcttatcgg gcagcatgtt gagttgcata atccaaaccc accacttcac     540
acagtgggtt acatacacac caagatgtct cctatggagg tggcaaggaa tgctagtgaa     600
gatgcaaggt cgatttgttt cagagagtat ggttctgctc cggagataaa catatatggc     660
gatccaagtt tcacttttcc gtatgttccg acccatttgc atcttatggt gtatgagtta     720
gtcaagaact ctctccgtgc tgtccaagag cggtttgttg actctgatag ggttgcacca     780
ccaatccgta tcattgttgc tgatggaatc gaagatgtta caataaaggt ctcagatgaa     840
ggtggaggta taccgagaag cggtctccct aaaatattca cttacctcta cagcactgca     900
```

-continued

```
agaaacccac ttgaagaaga tgtggacttg ggaaccgctg atgttcccct gactatggct      960
ggttatggtt atggtctgcc tattagtcgc ttgtatgctc gctatttggg tggagatttg     1020
cagatcatat ccatggaagg atacgggact gatgcttact tgcacttgtc tcgtcttgga     1080
gactcgcagg agcctttgcc atga                                            1104
```

<210> SEQ ID NO 2
<211> LENGTH: 1104
<212> TYPE: DNA
<213> ORGANISM: Brassica rapa
<220> FEATURE:
<223> OTHER INFORMATION: PDHK cDNA from B. rapa

<400> SEQUENCE: 2

```
atggcggtga agaaggctag cgagatgttt tcgaagagct tgatcgagga cgttcacaga      60
tggggatgca tgaagcagac gggcgtgagc ctcaggtaca tgatggagtt cggttccact     120
cccactgaga gaaaccttct gatctcggcg cagtttcttc acaaggagct tccgattcgg     180
atcgcgaggc gtgcgatcga actcgagacg ctgccttatg cctctctga  gaaacctgcc     240 gtcttgaagg tgagggattg gtatgtggag tcattcaggg acatgagagc gtttcctgag     300
atcaaggata ctgctgatga gaaagagttc actcagatga ttaaggctgt taaagtaagg     360
cacaacaacg tggttcccat gatggctctg ggtgtgaacc agctgaagaa aggaatgaaa     420
ctctacgaaa agcttgatga gattcatcag tttcttgatc gcttctactt gtctcgtata     480
gggatccgta tgcttatcgg gcagcatgtt gagttgcata atccaaaccc accacttcac     540
acagtgggtt acatacacac caagatgtct cctatggagg tggcaaggaa tgctagtgaa     600
gatgcaaggt cgatttgttt cagagagtat ggttctgctc cggagataaa catatatggc     660
gatccaagtt ccactyttcc gtatgttccg acccatttgc atcttatggt gtatgagtta     720
gtcaagaact ctctccgtgc tgtccaagag cggtttgttg actctgatag ggttgcacca     780
ccaatccgta tcattgttgc tgatggaatc gaagatgtta caataaaggt ctcagatgaa     840
ggtggaggta taccgagaag cggtctccct aaaatattca cttacctcta cagcactgca     900
agaaacccac ttgaagaaga tgtggacttg ggaaccgctg atgttcccct gactatggct     960
ggttatggtt atggtctgcc tattagtcgc ttgtatgctc gctatttggg tggagatttg    1020
cagatcatat ccatggaagg atacgggact gatgcttact tgcacttgtc tcgtcttgga    1080
gactcgcagg agcctttgcc atga                                           1104
```

<210> SEQ ID NO 3
<211> LENGTH: 1104
<212> TYPE: DNA
<213> ORGANISM: Brassica oleracea
<220> FEATURE:
<223> OTHER INFORMATION: PDHK cDNA from B. oleracea

<400> SEQUENCE: 3

```
atggcggtga agaaggctag cgagatgttt tcgaagagct tgatcgagga cgttcacaga      60
tggggatgca tgaagcagac gggcgtgagc ctcaggtaca tgatggagtt cggttccact     120
cccactgaga ggaacctcct gatctcggcg cagtttcttc acaaggagct tccgattcgg     180
atcgcgaggc gtgcgatcga actcgagacg ctgccttatg cctctctga  gaaacctgcc     240 gtcttgaagg taagrgattg gtatgtggag tcattcaggr acatgagagc gtttcctgag     300
atcaaggata ctgctgayga gaaagagttc acacagatga ttaaggctgt taaagtaagg     360
```

-continued

```
cacaacaacg tggttcccat gatggctctg ggtgttaacc agctgaagaa aggaatgaaa      420
ctctacgaaa aactcgatga gattcatcag tttcttgatc gcttctactt gtcacgtata      480
gggatccgta tgcttatcgg gcagcatgtt gagttgcata atccaaaccc accacttcac      540
actgtgggtt acatacacac caagatgtct cctatggagg tggcaaggaa tgcyagtgaa      600
gatgcaaggt cgatttgttt casagagtat ggttctgctc cggagataaa cmtatatggc      660
gatccaagtt tcacctttcc gtatgtacca acccatttgc atcttatggt gtatgagcta      720
gtcaagaact ctctacgtgc tgtccaagag cgatttgttg attctgatag ggttgcacca      780
ccaatccgta tcattgttgc tgatggaatc gaagatgtta caataaaggt ctcagatgaa      840
ggtggaggta taccgagaag cggtctgccc aaaatattca cttacctsta cagcactgca      900
agaaacccgc ttgaagaaga tgtggacttg gaacagctg atgtacccgt gacwatggct       960
ggttatggtt atggtctgcc yattagtcgc ttgtatgctc gatactttgg tggagatttg     1020
cagatcatat ccatggaagg atacgggact gatgcttact tgcacttgtc tcgtcttgga     1080
gactcgcaag agcctttgcc atga                                            1104
```

<210> SEQ ID NO 4
<211> LENGTH: 1104
<212> TYPE: DNA
<213> ORGANISM: Brassica carinata
<220> FEATURE:
<223> OTHER INFORMATION: PDHK cDNA from B. carinata

<400> SEQUENCE: 4

```
atggcggtga agaaggctag cgagatgttt tcgaagagct tgatcgagga cgttcacaga       60
tggggatgca tgaagcagac gggcgtgagc ctcaggtaca tgatggagtt cggttccact      120
cccactgaga ggaacctcct gatctcggcg cagtttcttc acaaggagct tccgattcgg      180
atcgcgaggc gtgcgatcga actcgagacg ctgccttatg gcctctctga aaacctgcc      240 gtcttgaagg taagagattg gtatgtggag tcattcaggg acatgagagc gtttcctgag      300
atcaaggata ctgctgatga aaagagttc acacagatga ttaaggctgt taaagtaagg      360
cacaacaacg tggttcccat gatggctctg ggtgttaacc agctgaagaa aggaatgaaa      420
ctctacgaaa aactcgatga gattcatcag ttttttgatc gcttctactt gtcacgtata      480
gggatccgta tgcttatcgg gcagcatgtt gagttgcata atccaaaccc accacttcac      540
actgtgggtt acatacacac caagatgtct ccaatggagg tggcaaggaa tgctagtgaa      600
gatgcaaggt cgatttgttt ccgagagtat ggttctgctc cggagataaa catatatggc      660
gatccaagtt tcacctttcc gtatgtacca acccatttgc atcttatggt gtatgagcta      720
gtcaagaact ctctacgtgc tgtccaagag cggtttgttg actctgatag ggttgcacca      780
ccaatccgta tcattgttgc tgatggaatc gaagatgtta caataaaggt ctcagatgaa      840
ggtggaggta taccgagaag cggcctgccc aaaatattca cttacctcta cagcactgca      900
agaaacccgc ttgaagaaga tgtggacttg gaacagctg atgtacccgt gactatggct       960
ggttatggtt atggtctgcc tattagtcgc ttgtatgctc gatactttgg tggagatttg     1020
cagatcatat ccatggaagg atacgggact gatgcttact tgcacttatc tcgtcttgga     1080
gactcgcagg agcctttgcc atga                                            1104
```

<210> SEQ ID NO 5
<211> LENGTH: 367
<212> TYPE: PRT
<213> ORGANISM: Brassica napus
<220> FEATURE:
<223> OTHER INFORMATION: Deduced amino acid sequence from B. napus PDHK cDNA (SEQ ID NO:1)

<400> SEQUENCE: 5

```
Met Ala Val Lys Lys Ala Ser Glu Met Phe Ser Lys Ser Leu Ile Glu
 1               5                  10                  15

Asp Val His Arg Trp Gly Cys Met Lys Gln Thr Gly Val Ser Leu Arg
            20                  25                  30

Tyr Met Met Glu Phe Gly Ser Thr Pro Thr Glu Arg Asn Leu Leu Ile
         35                  40                  45

Ser Ala Gln Phe Leu His Lys Glu Leu Pro Ile Arg Ile Ala Arg Arg
     50                  55                  60

Ala Ile Glu Leu Glu Thr Leu Pro Tyr Gly Leu Ser Glu Lys Pro Ala
65                  70                  75                  80

Val Leu Lys Val Arg Asp Trp Tyr Val Glu Ser Phe Arg Asp Met Arg
                85                  90                  95

Ala Phe Pro Glu Ile Lys Asp Thr Ala Asp Glu Lys Glu Phe Thr Gln
            100                 105                 110

Met Ile Lys Ala Val Lys Val Arg His Asn Asn Val Val Pro Met Met
        115                 120                 125

Ala Leu Gly Val Asn Gln Leu Lys Lys Gly Met Lys Leu Tyr Glu Lys
130                 135                 140

Leu Asp Glu Ile His Gln Phe Leu Asp Arg Phe Tyr Leu Ser Arg Ile
145                 150                 155                 160

Gly Ile Arg Met Leu Ile Gly Gln His Val Glu Leu His Asn Pro Asn
                165                 170                 175

Pro Pro Leu His Thr Val Gly Tyr Ile His Thr Lys Met Ser Pro Met
            180                 185                 190

Glu Val Ala Arg Asn Ala Ser Glu Asp Ala Arg Ser Ile Cys Phe Arg
        195                 200                 205

Glu Tyr Gly Ser Ala Pro Glu Ile Asn Ile Tyr Gly Asp Pro Ser Phe
210                 215                 220

Thr Phe Pro Tyr Val Pro Thr His Leu His Leu Met Val Tyr Glu Leu
225                 230                 235                 240

Val Lys Asn Ser Leu Arg Ala Val Gln Glu Arg Phe Val Asp Ser Asp
                245                 250                 255

Arg Val Ala Pro Pro Ile Arg Ile Ile Val Ala Asp Gly Ile Glu Asp
            260                 265                 270

Val Thr Ile Lys Val Ser Asp Glu Gly Gly Ile Pro Arg Ser Gly
        275                 280                 285

Leu Pro Lys Ile Phe Thr Tyr Leu Tyr Ser Thr Ala Arg Asn Pro Leu
290                 295                 300

Glu Glu Asp Val Asp Leu Gly Thr Ala Asp Val Pro Leu Thr Met Ala
305                 310                 315                 320

Gly Tyr Gly Tyr Gly Leu Pro Ile Ser Arg Leu Tyr Ala Arg Tyr Phe
                325                 330                 335

Gly Gly Asp Leu Gln Ile Ile Ser Met Glu Gly Tyr Gly Thr Asp Ala
            340                 345                 350

Tyr Leu His Leu Ser Arg Leu Gly Asp Ser Gln Glu Pro Leu Pro
        355                 360                 365
```

<210> SEQ ID NO 6
<211> LENGTH: 367
<212> TYPE: PRT

<213> ORGANISM: Brassica rapa
<220> FEATURE:
<223> OTHER INFORMATION: Deduced amino acid sequence from B. rapa PDHK cDNA (SEQ ID NO:2)

<400> SEQUENCE: 6

```
Met Ala Val Lys Lys Ala Ser Glu Met Phe Ser Lys Ser Leu Ile Glu
1               5                   10                  15

Asp Val His Arg Trp Gly Cys Met Lys Gln Thr Gly Val Ser Leu Arg
            20                  25                  30

Tyr Met Met Glu Phe Gly Ser Thr Pro Thr Glu Arg Asn Leu Leu Ile
        35                  40                  45

Ser Ala Gln Phe Leu His Lys Glu Leu Pro Ile Arg Ile Ala Arg Arg
    50                  55                  60

Ala Ile Glu Leu Glu Thr Leu Pro Tyr Gly Leu Ser Glu Lys Pro Ala
65                  70                  75                  80

Val Leu Lys Val Arg Asp Trp Tyr Val Glu Ser Phe Arg Asp Met Arg
                85                  90                  95

Ala Phe Pro Glu Ile Lys Asp Thr Ala Asp Glu Lys Glu Phe Thr Gln
            100                 105                 110

Met Ile Lys Ala Val Lys Val Arg His Asn Asn Val Pro Met Met
        115                 120                 125

Ala Leu Gly Val Asn Gln Leu Lys Lys Gly Met Lys Leu Tyr Glu Lys
    130                 135                 140

Leu Asp Glu Ile His Gln Phe Leu Asp Arg Phe Tyr Leu Ser Arg Ile
145                 150                 155                 160

Gly Ile Arg Met Leu Ile Gly Gln His Val Glu Leu His Asn Pro Asn
                165                 170                 175

Pro Pro Leu His Thr Val Gly Tyr Ile His Thr Lys Met Ser Pro Met
            180                 185                 190

Glu Val Ala Arg Asn Ala Ser Glu Asp Ala Arg Ser Ile Cys Phe Arg
        195                 200                 205

Glu Tyr Gly Ser Ala Pro Glu Ile Asn Ile Tyr Gly Asp Pro Ser Ser
    210                 215                 220

Thr Phe Pro Tyr Val Pro Thr His Leu His Leu Met Val Tyr Glu Leu
225                 230                 235                 240

Val Lys Asn Ser Leu Arg Ala Val Gln Glu Arg Phe Val Asp Ser Asp
                245                 250                 255

Arg Val Ala Pro Pro Ile Arg Ile Ile Val Ala Asp Gly Ile Glu Asp
            260                 265                 270

Val Thr Ile Lys Val Ser Asp Glu Gly Gly Gly Ile Pro Arg Ser Gly
        275                 280                 285

Leu Pro Lys Ile Phe Thr Tyr Leu Tyr Ser Thr Ala Arg Asn Pro Leu
    290                 295                 300

Glu Glu Asp Val Asp Leu Gly Thr Ala Asp Val Pro Leu Thr Met Ala
305                 310                 315                 320

Gly Tyr Gly Tyr Gly Leu Pro Ile Ser Arg Leu Tyr Ala Arg Tyr Phe
                325                 330                 335

Gly Gly Asp Leu Gln Ile Ile Ser Met Glu Gly Tyr Gly Thr Asp Ala
            340                 345                 350

Tyr Leu His Leu Ser Arg Leu Gly Asp Ser Gln Glu Pro Leu Pro
        355                 360                 365
```

<210> SEQ ID NO 7
<211> LENGTH: 367

```
<212> TYPE: PRT
<213> ORGANISM: Brassica oleracea
<220> FEATURE:
<221> NAME/KEY: misc_feature
<222> LOCATION: (94)..(94)
<223> OTHER INFORMATION: X at position 94 is N or D
<220> FEATURE:
<223> OTHER INFORMATION: Deduced amino acid sequence from B. oleracea
      PDHK cDNA (SEQ ID NO:3).

<400> SEQUENCE: 7
```

| | | | | | | | | | | | | | | | |
|---|---|---|---|---|---|---|---|---|---|---|---|---|---|---|---|
| Met | Ala | Val | Lys | Lys | Ala | Ser | Glu | Met | Phe | Ser | Lys | Ser | Leu | Ile | Glu |
| 1 | | | | 5 | | | | | 10 | | | | | 15 | |
| Asp | Val | His | Arg | Trp | Gly | Cys | Met | Lys | Gln | Thr | Gly | Val | Ser | Leu | Arg |
| | | | 20 | | | | | 25 | | | | | 30 | | |
| Tyr | Met | Met | Glu | Phe | Gly | Ser | Thr | Pro | Thr | Glu | Arg | Asn | Leu | Leu | Ile |
| | | 35 | | | | | 40 | | | | | 45 | | | |
| Ser | Ala | Gln | Phe | Leu | His | Lys | Glu | Leu | Pro | Ile | Arg | Ile | Ala | Arg | Arg |
| | 50 | | | | | 55 | | | | | 60 | | | | |
| Ala | Ile | Glu | Leu | Glu | Thr | Leu | Pro | Tyr | Gly | Leu | Ser | Glu | Lys | Pro | Ala |
| 65 | | | | | 70 | | | | | 75 | | | | | 80 |
| Val | Leu | Lys | Val | Arg | Asp | Trp | Tyr | Val | Glu | Ser | Phe | Arg | Xaa | Met | Arg |
| | | | | 85 | | | | | 90 | | | | | 95 | |
| Ala | Phe | Pro | Glu | Ile | Lys | Asp | Thr | Ala | Asp | Glu | Lys | Glu | Phe | Thr | Gln |
| | | | 100 | | | | | 105 | | | | | 110 | | |
| Met | Ile | Lys | Ala | Val | Lys | Val | Arg | His | Asn | Asn | Val | Val | Pro | Met | Met |
| | | 115 | | | | | 120 | | | | | 125 | | | |
| Ala | Leu | Gly | Val | Asn | Gln | Leu | Lys | Lys | Gly | Met | Lys | Leu | Tyr | Glu | Lys |
| | 130 | | | | | 135 | | | | | 140 | | | | |
| Leu | Asp | Glu | Ile | His | Gln | Phe | Leu | Asp | Arg | Phe | Tyr | Leu | Ser | Arg | Ile |
| 145 | | | | | 150 | | | | | 155 | | | | | 160 |
| Gly | Ile | Arg | Met | Leu | Ile | Gly | Gln | His | Val | Glu | Leu | His | Asn | Pro | Asn |
| | | | | 165 | | | | | 170 | | | | | 175 | |
| Pro | Pro | Leu | His | Thr | Val | Gly | Tyr | Ile | His | Thr | Lys | Met | Ser | Pro | Met |
| | | | 180 | | | | | 185 | | | | | 190 | | |
| Glu | Val | Ala | Arg | Asn | Ala | Ser | Glu | Asp | Ala | Arg | Ser | Ile | Cys | Phe | Arg |
| | | 195 | | | | | 200 | | | | | 205 | | | |
| Glu | Tyr | Gly | Ser | Ala | Pro | Glu | Ile | Asn | Ile | Tyr | Gly | Asp | Pro | Ser | Phe |
| | 210 | | | | | 215 | | | | | 220 | | | | |
| Thr | Phe | Pro | Tyr | Val | Pro | Thr | His | Leu | His | Leu | Met | Val | Tyr | Glu | Leu |
| 225 | | | | | 230 | | | | | 235 | | | | | 240 |
| Val | Lys | Asn | Ser | Leu | Arg | Ala | Val | Gln | Glu | Arg | Phe | Val | Asp | Ser | Asp |
| | | | | 245 | | | | | 250 | | | | | 255 | |
| Arg | Val | Ala | Pro | Pro | Ile | Arg | Ile | Ile | Val | Ala | Asp | Gly | Ile | Glu | Asp |
| | | | 260 | | | | | 265 | | | | | 270 | | |
| Val | Thr | Ile | Lys | Val | Ser | Asp | Glu | Gly | Gly | Gly | Ile | Pro | Arg | Ser | Gly |
| | | 275 | | | | | 280 | | | | | 285 | | | |
| Leu | Pro | Lys | Ile | Phe | Thr | Tyr | Leu | Tyr | Ser | Thr | Ala | Arg | Asn | Pro | Leu |
| | 290 | | | | | 295 | | | | | 300 | | | | |
| Glu | Glu | Asp | Val | Asp | Leu | Gly | Thr | Ala | Asp | Pro | Val | Thr | Met | Ala | |
| 305 | | | | | 310 | | | | | 315 | | | | | 320 |
| Gly | Tyr | Gly | Tyr | Gly | Leu | Pro | Ile | Ser | Arg | Leu | Tyr | Ala | Arg | Tyr | Phe |
| | | | | 325 | | | | | 330 | | | | | 335 | |
| Gly | Gly | Asp | Leu | Gln | Ile | Ile | Ser | Met | Glu | Gly | Tyr | Gly | Thr | Asp | Ala |
| | | | 340 | | | | | 345 | | | | | 350 | | |
| Tyr | Leu | His | Leu | Ser | Arg | Leu | Gly | Asp | Ser | Gln | Glu | Pro | Leu | Pro | |

|  | 355 | 360 | 365 |
|---|---|---|---|

<210> SEQ ID NO 8
<211> LENGTH: 367
<212> TYPE: PRT
<213> ORGANISM: Brassica carinata
<220> FEATURE:
<223> OTHER INFORMATION: Deduced amino acid sequence from B. carinata
      PDHK cDNA (SEQ ID NO:4).

<400> SEQUENCE: 8

Met Ala Val Lys Lys Ala Ser Glu Met Phe Ser Lys Ser Leu Ile Glu
1               5                   10                  15

Asp Val His Arg Trp Gly Cys Met Lys Gln Thr Gly Val Ser Leu Arg
            20                  25                  30

Tyr Met Met Glu Phe Gly Ser Thr Pro Thr Glu Arg Asn Leu Leu Ile
        35                  40                  45

Ser Ala Gln Phe Leu His Lys Glu Leu Pro Ile Arg Ile Ala Arg Arg
    50                  55                  60

Ala Ile Glu Leu Glu Thr Leu Pro Tyr Gly Leu Ser Glu Lys Pro Ala
65                  70                  75                  80

Val Leu Lys Val Arg Asp Trp Tyr Val Glu Ser Phe Arg Asp Met Arg
                85                  90                  95

Ala Phe Pro Glu Ile Lys Asp Thr Ala Asp Glu Lys Glu Phe Thr Gln
            100                 105                 110

Met Ile Lys Ala Val Lys Val Arg His Asn Asn Val Val Pro Met Met
        115                 120                 125

Ala Leu Gly Val Asn Gln Leu Lys Lys Gly Met Lys Leu Tyr Glu Lys
    130                 135                 140

Leu Asp Glu Ile His Gln Phe Phe Asp Arg Phe Tyr Leu Ser Arg Ile
145                 150                 155                 160

Gly Ile Arg Met Leu Ile Gly Gln His Val Glu Leu His Asn Pro Asn
                165                 170                 175

Pro Pro Leu His Thr Val Gly Tyr Ile His Thr Lys Met Ser Pro Met
            180                 185                 190

Glu Val Ala Arg Asn Ala Ser Glu Asp Ala Arg Ser Ile Cys Phe Arg
        195                 200                 205

Glu Tyr Gly Ser Ala Pro Glu Ile Asn Ile Tyr Gly Asp Pro Ser Phe
    210                 215                 220

Thr Phe Pro Tyr Val Pro Thr His Leu His Leu Met Val Tyr Glu Leu
225                 230                 235                 240

Val Lys Asn Ser Leu Arg Ala Val Gln Glu Arg Phe Val Asp Ser Asp
                245                 250                 255

Arg Val Ala Pro Pro Ile Arg Ile Ile Val Ala Asp Gly Ile Glu Asp
            260                 265                 270

Val Thr Ile Lys Val Ser Asp Glu Gly Gly Ile Pro Arg Ser Gly
        275                 280                 285

Leu Pro Lys Ile Phe Thr Tyr Leu Tyr Ser Thr Ala Arg Asn Pro Leu
    290                 295                 300

Glu Glu Asp Val Asp Leu Gly Thr Ala Asp Val Pro Val Thr Met Ala
305                 310                 315                 320

Gly Tyr Gly Tyr Gly Leu Pro Ile Ser Arg Leu Tyr Ala Arg Tyr Phe
                325                 330                 335

Gly Gly Asp Leu Gln Ile Ile Ser Met Glu Gly Tyr Gly Thr Asp Ala
            340                 345                 350

```
Tyr Leu His Leu Ser Arg Leu Gly Asp Ser Gln Glu Pro Leu Pro
        355                 360                 365
```

<210> SEQ ID NO 9
<211> LENGTH: 27
<212> TYPE: DNA
<213> ORGANISM: Artificial
<220> FEATURE:
<223> OTHER INFORMATION: Degenerate forward primer with a KpnI site
      designed from conserved segments of known PDHK amino-acid
      sequences from Arabidopsis (CAA07447) and corn (AF038585).
<220> FEATURE:
<221> NAME/KEY: misc_feature
<222> LOCATION: (15)..(15)
<223> OTHER INFORMATION: N at position 15 is a mix of A, T, G and C
<220> FEATURE:
<221> NAME/KEY: misc_feature
<222> LOCATION: (16)..(16)
<223> OTHER INFORMATION: N at position 16 = is a mix of A, T, G and C

<400> SEQUENCE: 9
cggggtacct ggggnnssat gaarcar                                       27

<210> SEQ ID NO 10
<211> LENGTH: 27
<212> TYPE: DNA
<213> ORGANISM: Artificial
<220> FEATURE:
<223> OTHER INFORMATION: Degenerate reverse primer with a XbaI site
      designed from conserved segments of known PDHK amino-acid
      sequences from Arabidopsis (CAA07447) and corn (AF038585).
<220> FEATURE:
<221> NAME/KEY: misc_feature
<222> LOCATION: (13)..(13)
<223> OTHER INFORMATION: N at position 13 is a mix of A, T, G and C

<400> SEQUENCE: 10
tgctctagat yanggyaarg gytcyts                                       27

<210> SEQ ID NO 11
<211> LENGTH: 21
<212> TYPE: DNA
<213> ORGANISM: Artificial
<220> FEATURE:
<223> OTHER INFORMATION: 5'RACE GSP1 gene specific primer designed from
      the DNA sequence information provided by RACE-generated fragments.

<400> SEQUENCE: 11
ctttcttcag ctggttcaca c                                             21

<210> SEQ ID NO 12
<211> LENGTH: 29
<212> TYPE: DNA
<213> ORGANISM: Artificial
<220> FEATURE:
<223> OTHER INFORMATION: 5'RACE GSP2 gene specific primer designed from
      the DNA sequence information provided by RACE-generated fragments.

<400> SEQUENCE: 12
gactccacat accaatctct taccttcaa                                     29

<210> SEQ ID NO 13
<211> LENGTH: 23
<212> TYPE: DNA
<213> ORGANISM: Artificial
<220> FEATURE:
<223> OTHER INFORMATION: 5'RACE GSP3 gene specific primer designed from
      the DNA sequence information provided by RACE-generated fragments.

-continued

```
<400> SEQUENCE: 13
cataaggcag cgtctcgagt tcg                                              23

<210> SEQ ID NO 14
<211> LENGTH: 25
<212> TYPE: DNA
<213> ORGANISM: Artificial
<220> FEATURE:
<223> OTHER INFORMATION: 3'RACE GSP1 gene specific primer designed from
      the DNA sequence information provided by RACE-generated fragments.

<400> SEQUENCE: 14
agatgtggac ttgggaaccg ctgat                                            25

<210> SEQ ID NO 15
<211> LENGTH: 28
<212> TYPE: DNA
<213> ORGANISM: Artificial
<220> FEATURE:
<223> OTHER INFORMATION: 3'RACE GSP2 gene specific primer designed from
      the DNA sequence information provided by RACE-generated fragments.

<400> SEQUENCE: 15
gttatggtct gcctattagt cgcttgta                                         28

<210> SEQ ID NO 16
<211> LENGTH: 24
<212> TYPE: DNA
<213> ORGANISM: Artificial
<220> FEATURE:
<223> OTHER INFORMATION: Forward primer designed to add a PmeI
      restriction site to one end of the PDHK gene

<400> SEQUENCE: 16
gtttaaacat ggcggtgaag aagg                                             24

<210> SEQ ID NO 17
<211> LENGTH: 24
<212> TYPE: DNA
<213> ORGANISM: Artificial
<220> FEATURE:
<223> OTHER INFORMATION: Reverse primer designed to add a PmeI
      restriction site to one end of the PDHK gene

<400> SEQUENCE: 17
gtttaaactc atggcaaagg ctcc                                             24

<210> SEQ ID NO 18
<211> LENGTH: 25
<212> TYPE: DNA
<213> ORGANISM: Artificial
<220> FEATURE:
<223> OTHER INFORMATION: Forward primer designed to add two restriction
      sites, BstE II and BsiW, at each end of teh Bn PDHK gene

<400> SEQUENCE: 18
cgtacgatgg cggtgaagaa ggcta                                            25

<210> SEQ ID NO 19
<211> LENGTH: 24
<212> TYPE: DNA
```

```
<213> ORGANISM: Artificial
<220> FEATURE:
<223> OTHER INFORMATION: Reverse primer designed to add two restriction
      sites, BstE II and BsiW, at each end of teh Bn PDHK gene

<400> SEQUENCE: 19
ggtgacctca tggcaaaggc tcct                                              24
```

BRASSICA PYRUVATE DEHYDROGENASE KINASE GENE

CROSS-REFERENCE TO RELATED APPLICATIONS

This application is a continuation-in-part of U.S. patent application Ser. No. 10/222,075, filed Aug. 16, 2002, now U.S. Pat. No. 7,057,091 B2, the contents of which are incorporated herein in its entirety.

TECHNICAL FIELD

This invention relates to plant genes useful for the genetic manipulation of plant characteristics. More specifically, the invention relates to the identification, isolation, and introduction of genes of *Brassica* PDHK sequences.

BACKGROUND

As described in FIG. 1 of PCT International Patent Application PCT/CA98/00096 to Zou and Taylor, (PCT International Publication WO 98/35044 published Aug. 13, 1998, the contents of the entirety of which and the corresponding U.S. patent application Ser. No. 09/355,912, filed Oct. 15, 1999, are incorporated by this reference), acetyl-CoA plays a central role in mitochondrial respiration and plastidial fatty acid biosynthesis. The pyruvate dehydrogenase complex (PDC) oxidatively decarboxylates pyruvate to yield acetyl-CoA.

Plants have both mitochondrial and plastidial isoforms of the PDC (see also U.S. Pat. No. 6,265,636, to Randall et al (Jul. 24, 2001); which is also incorporated in its entirety by this reference). The mitochondrial pyruvate dehydrogenase complex plays a key role in the regulation of acetyl-CoA generation and availability of acetyl moieties for various catabolic and anabolic reactions in plant cells. The mitochondrial PDC is negatively regulated by phosphorylation of the E1α subunit by pyruvate dehydrogenase kinase (PDHK), and positively regulated by dephosphorylation of the PDC by pyruvate dehydrogenase phosphatase (PDCP). Mitochondrially-generated acetyl moieties can find their way into the respiratory tricarboxylic acid (TCA; Krebs) cycle, but also into the plastid compartment where ultimately, acetate units are used by the enzymes of the fatty acid synthesis (FAS) pathway to synthesize fatty acids. These are eventually incorporated into membrane and also storage glycerolipids.

Zou and Taylor also disclose the identification, isolation and characterization of the pyruvate dehydrogenase kinase (PDHK) (gene and cDNA) sequence from the model plant system *Arabidopsis thaliana* and the utilization of this sequence in the genetic manipulation of plants. Also disclosed is a vector containing the full-length PDHK sequence or a significant portion of the PDHK sequence from *Arabidopsis*, in an anti-sense orientation under control of either a constitutive or a seed-specific promoter, for re-introducing into *Arabidopsis* or for introducing into other plants. Zou and Taylor also provided a method to construct a vector containing the full-length PDHK sequence or a significant portion of the PDHK sequence from *Arabidopsis*, in a sense orientation under control of either a constitutive or a seed-specific promoter, for re-introducing into *Arabidopsis* or for introducing into other plants. Also disclosed were methods for modifying *Arabidopsis* and other plants to change their seed oil content, average seed weight or size, respiration rate during development, vegetative growth characteristics, flowering time or patterns of generative growth, and the period required to reach seed maturity.

As disclosed in, for example, Zou and Taylor, respiration, which involves the consumption of $O_2$ and the catabolism of sugar or other substrates to produce $CO_2$, plays a central role in the process of plant growth in providing reducing equivalents, a source of energy and an array of intermediates (carbon skeletons) as the building blocks for many essential biosynthetic processes. The intermediate products of respiration are necessary for growth in meristematic tissues, maintenance of existing phytomass, uptake of nutrients, and intra- and inter-cellular transport of organic and inorganic materials. Respiration is important to both anabolic and catabolic phases of metabolism.

The pyruvate dehydrogenase complex (PDC) is a particularly important site for regulation of plant respiration. Modification of PDC activity through manipulation of PDHK expression can result in a change in the production or availability of mitochondrially-generated acetyl-CoA or a change in the respiration rate. These changes may in turn affect seed oil content, average seed weight or size, respiration rate during development, vegetative growth characteristics, flowering time or patterns of generative growth, and the period required to reach seed maturity.

Many examples exist of successful modifications to plant metabolism that have been achieved by genetic engineering to transfer new genes or to alter the expression of existing genes, in plants. It is now routinely possible to introduce genes into many plant species of agronomic significance to improve crop performance (e.g., seed oil or tuber starch content/composition; meal improvement; herbicide, disease or insect resistance; heavy metal tolerance; etc.) (Somerville, 1993; Kishore and Somerville, 1993; MacKenzie and Jain, 1997).

The *Brassica* genus includes *Arabidopsis thaliana*. The Brassicaceae family is comprised of a large and diverse group of plant species which are economically very important throughout the world. Three diploid *Brassica* species (*B. rapa, B. oleracea* and *B. nigra*) have hybridized in different combinations to give rise to the three amphidiploid species (*B. napus, B. juncea*, and *B. carinata*). Other *Brassica* species include *B. oleifera, B. balearica, B. cretica, B. elongate, B. tourneforii,* and *B. biennis. B. napus* and *B. rapa* have been improved through breeding programs and are now cultivated as canola crops.

It would be an improvement in the art to isolate and sequence the PDHK gene from various useful species of plants of the Brassicaceae.

SUMMARY OF THE INVENTION

The invention involves the isolation, and characterization of PDHK (gene and cDNA) sequences from *Brassica* species and the utilization of these sequences in the genetic manipulation of plants.

The invention also discloses a vector containing the full-length PDHK sequence or a significant portion of PDHK sequences from the Brassicaceae, in an anti-sense orientation under control of either a constitutive or a seed-specific promoter, for re-introduction into *Brassica* species or for introduction into other plants.

The invention further describes a method to construct a vector containing the full-length PDHK sequence or a significant portion of the PDHK sequence from *Brassica* species, in a sense orientation under control of either a constitutive or a seed-specific promoter, for re-introducing into *Brassica* or for introduction into other plants.

The invention also provides methods of modifying Brassica and other plants to change their seed oil content, average seed weight or size, respiration rate during development, vegetative growth characteristics, flowering time or patterns of generative growth, and the period required to reach seed maturity.

According to one aspect of the present invention, there is disclosed isolated and purified deoxyribonucleic acid (DNA) of SEQ ID NO:1, SEQ ID NO:2, SEQ ID NO:3, and/or SEQ ID NO:4. In this aspect, SEQ ID NO:1 is the nucleotide sequence and the corresponding amino acid sequence (SEQ ID NO:5) of the *Brassica napus* PDHK cDNA. SEQ ID NO:2 is the nucleotide sequence and its corresponding amino acid sequence (SEQ ID NO:6) of the *Brassica rapa* PDHK cDNA. SEQ ID NO:3 is the nucleotide sequence and the corresponding amino acid sequence (SEQ ID NO:7) of the *Brassica oleracea* PDHK cDNA. SEQ ID NO:4 is the nucleotide sequence and the corresponding amino acid sequence (SEQ ID NO:8) of the *Brassica carinata* PDHK cDNA.

In yet another aspect of the invention, there is described a vector containing one or more of SEQ ID NO:1, SEQ ID NO:2, SEQ ID NO:3, or SEQ ID NO:4, or a part thereof, for introduction of the gene, in an anti-sense orientation into a plant cell, and a method for preparing a vector containing one or more of SEQ ID NO:1, SEQ ID NO:2, SEQ ID NO:3, or SEQ ID NO:4, or a part thereof, for introduction of the gene in a sense orientation, into a plant cell.

The invention also relates to transgenic plants and plant seeds having a genome containing an introduced DNA sequence of one or more of SEQ ID NO:1, SEQ ID NO:2, SEQ ID NO:3, or SEQ ID NO:4, or a part thereof, and a method of producing such plants and plant seeds.

The invention also relates to substantially homologous DNA sequences from plants with deduced amino acid sequences of 25% or greater identity, and 50% or greater similarity, isolated and/or characterized by known methods using the sequence information of SEQ ID NO:1, SEQ ID NO:2, SEQ ID NO:3, or SEQ ID NO:4, as will be appreciated by persons skilled in the art, and to parts of reduced length that are still able to function as inhibitors of gene expression by use in an anti-sense or co-suppression (Jorgensen and Napoli 1994) application. It will be appreciated by persons skilled in the art that small changes in the identities of nucleotides in a specific gene sequence may result in reduced or enhanced effectiveness of the genes and that, in some applications (e.g., anti-sense or co-suppression), partial sequences often work as effectively as full length versions. The ways in which the gene sequence can be varied or shortened are well known to persons skilled in the art, as are ways of testing the effectiveness of the altered genes. All such variations of the genes are therefore claimed as part of the present invention.

Stated more generally, the present invention relates to the isolation, purification and characterization of a mitochondrial pyruvate dehydrogenase kinase (PDHK) genes from the Brassicaceae (specifically *Brassica napus, B. rapa, B. oleracea*, and *B. carinata*) and identifies its utility in regulating fatty acid synthesis, seed oil content, seed size/weight, flowering time, vegetative growth, respiration rate and generation time.

The PDHK of the invention is useful in manipulating PDC activity and the respiration rate in plants. For example, as disclosed in Zou and Taylor, transforming plants with a construct containing the partial PDHK gene in an anti-sense orientation controlled by a constitutive promoter can result in increased mitochondrial PDC activity, an increased production or availability of mitochondrially-generated acetyl-CoA, and hence, an increased respiration rate.

Additionally, over-expressing the full-length PDHK in a sense orientation may reduce the activity of mitochondrial PDC, resulting in decreased respiratory rates in tissues, such as leaves or tubers, to decrease maintenance respiration and thereby increase the accumulation of biomass.

Some of the manipulations and deliverables which are possible using the PDHK gene or a part thereof, include, but are not limited to, the following: seeds with increased or decreased fatty acid and oil content; plants exhibiting early or delayed flowering times (measured in terms of days after planting or sowing seed); plants with increased or decreased vegetative growth (biomass); plants with root systems better able to withstand low soil temperatures or frost; plants with tissues exhibiting higher or lower rates of respiration; plants exhibiting an enhanced capacity to accumulate storage compounds in other storage organs (e.g., tubers); plants exhibiting an enhanced capacity to accumulate biopolymers which rely on acetyl moieties as precursors, such a polyhydroxyalkanoic acids or polyhydroxybutyric acids (Padgette et al., 1997).

In another exemplary embodiment, the invention discloses a genetically transformed plant having a means for modulating mitochondrially generated acetyl-CoA and/or respiration rate in the genetically transformed plant, wherein the means is operatively linked to a promoter.

In a further exemplary embodiment, the invention involves a process for modulating mitochondrially generated acetyl-CoA and/or respiration rate in a transgenic plant. The process includes cloning a gene encoding a *Brassica* pyruvate dehydrogenase kinase protein into a vector, positioning the gene in an anti-sense orientation, and transforming a plant with the vector.

An additional process for modulating mitochondrially generated acetyl-CoA and/or respiration rate is disclosed in an additional exemplary embodiment. The process includes cloning a gene encoding a *Brassica* pyruvate dehydrogenase kinase protein into a vector, reducing production of the *Brassica* pyruvate dehydrogenase kinase protein, and transforming the vector into a plant.

BEST MODE FOR CARRYING OUT THE INVENTION

Figure 1:
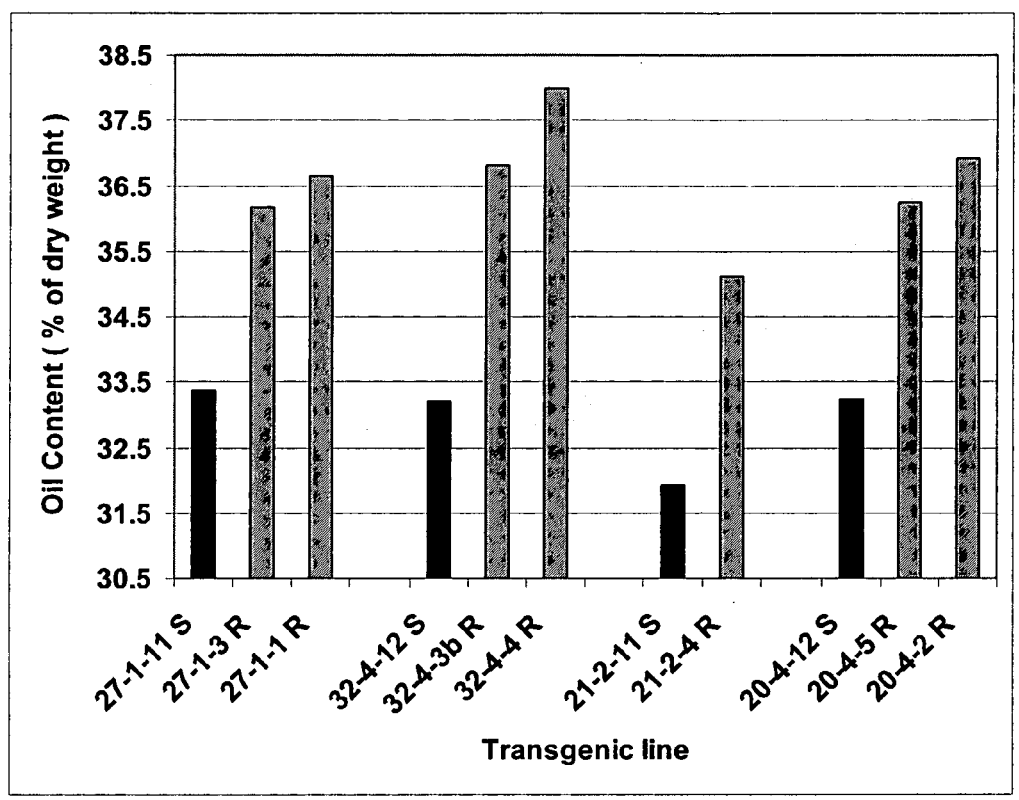
FIG. 1. Oil content (% of seed dry weight) of $T_3$ seed from *B. napus* cv NEX710 transgenic lines transformed with the *B. napus* Phaseolin:Antisense PDHK construct (R) compared to the oil content of seeds from their corresponding sibling null (S) control plants. Each value represents the average of three determinations.
Figure 2:
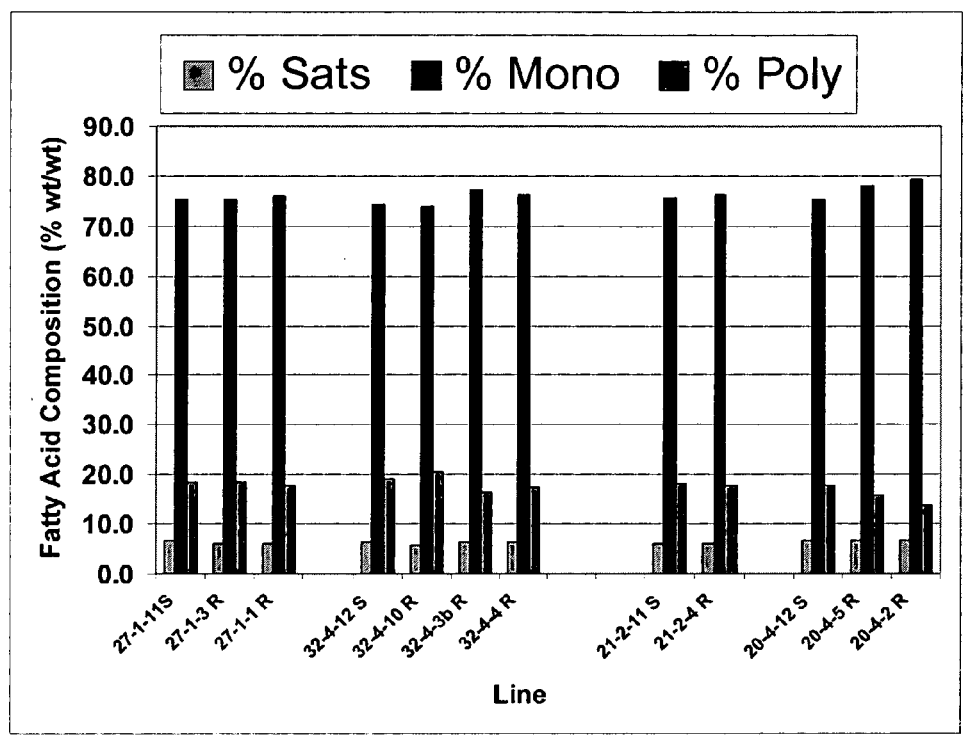
FIG. 2. Fatty acid composition of $T_3$ seed oil from *B. napus* cv NEX710 transgenic lines transformed with the *B. napus* Phaseolin:Antisense PDHK construct (R) compared to the fatty acid composition of seed oil from their corresponding sibling null (S) control plants. % Sats=% of total saturated fatty acids (hatched bars); % Mono=% of total monounsaturated fatty acids (black bars); % Poly=% total polyunsaturated fatty acids (speckled bars). Each value represents the average of three determinations.
Figure 3:
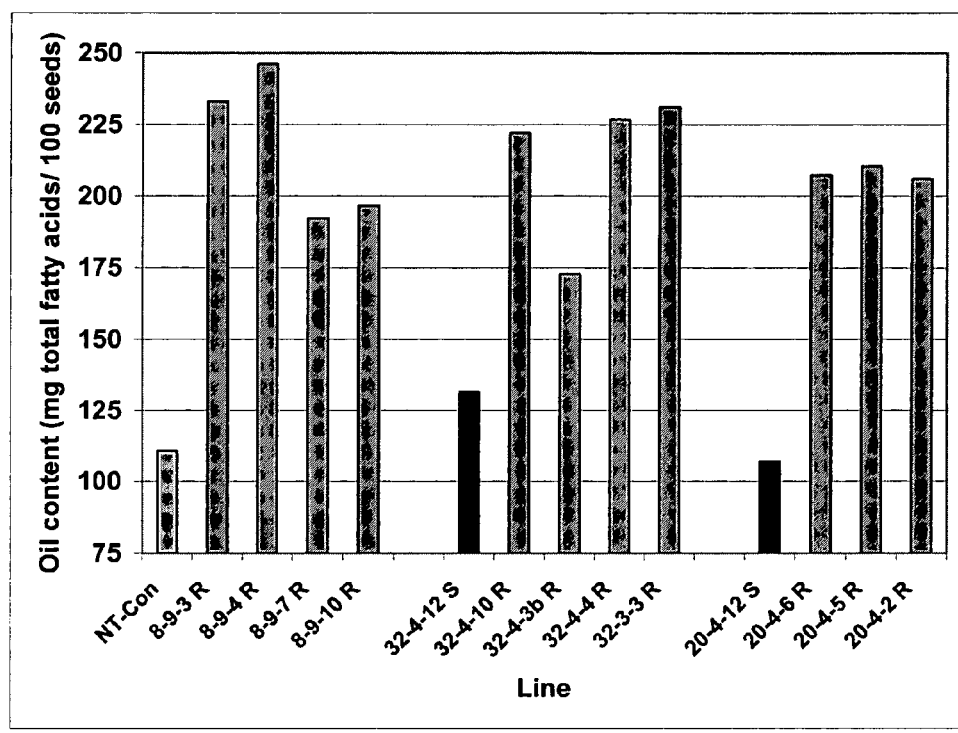
FIG. 3. Oil content (mg total fatty acids/100 seeds) of $T_3$ seed from *B. napus* cv NEX710 transgenic lines transformed with the *B. napus* Phaseolin:Antisense PDHK construct (R; hatched bars) compared to the oil content of seeds from their corresponding sibling null (S; black bars) or non-transformed (NT-Con; grey bar) control plants. Each value represents the average of three determinations.
Figure 4:
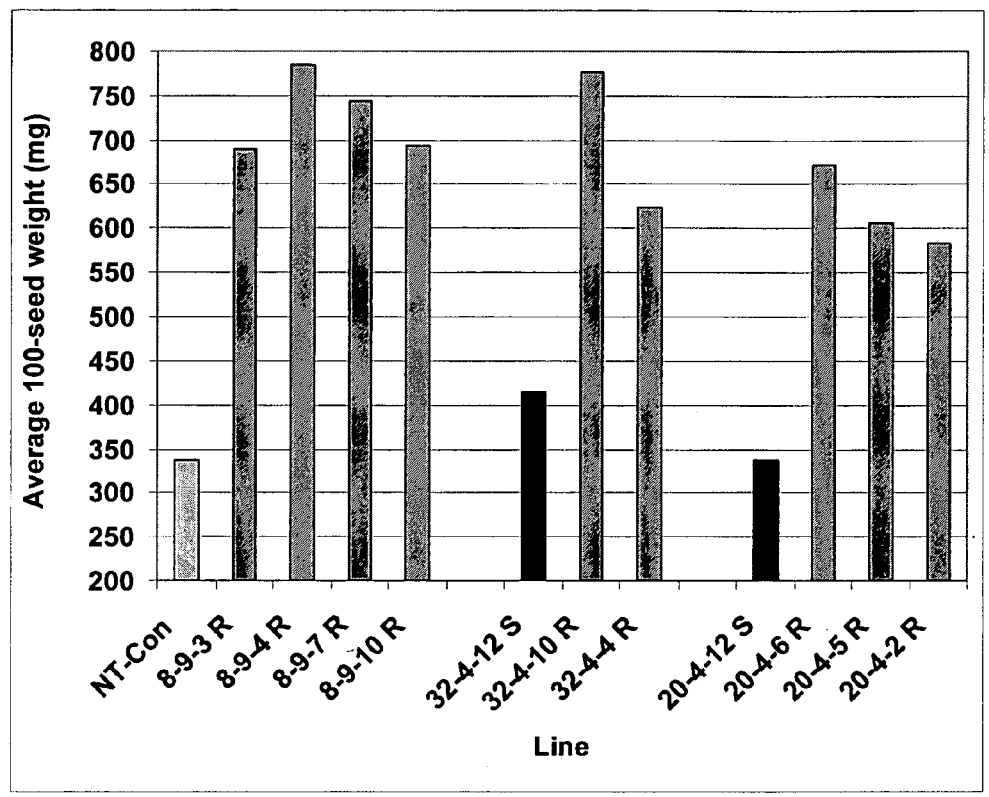
FIG. 4. Average 100-seed weight (mg) of T₃ seed from *B. napus* cv NEX710 transgenic lines transformed with the *B. napus* Phaseolin:Antisense PDHK construct (R; hatched bars) compared to the oil content of seeds from their corresponding sibling null (S; black bars) or non-transformed (NT-Con; grey bar) control plants. Each value represents the average of three determinations.

The best modes for carrying out the invention are apparent from PCT/CA98/00096 (PCT International Publication WO98/35044), incorporated herein, and from the following description of the results of tests and experiments that have been carried out by the inventors. Related technology is disclosed in the incorporated U.S. Pat. No. 6,265,636 to Randall et al.

All plant cells undergo mitochondrial respiration and this ubiquitous process is affected by the activity of the PDC and its regulators PDHK and PDCP. As disclosed in Zou and Taylor, manipulation of PDHK activity through silencing mechanisms (e.g. anti-sense RNA technology) using plant transformation can affect, e.g., PDH activity, mitochondrial respiration, seed oil content, flowering time, and growth rate.

A number of ways exist by which genes and gene constructs can be introduced into plants, and a combination of plant transformation and tissue culture techniques have been successfully integrated into effective strategies for creating transgenic crop plants. These methods, which can be used in the present invention, have been extensively reviewed elsewhere (Potrykus, 1991; Vasil, 1994; Walden and Wingender, 1995; Songstad et al., 1995), and are well known to persons skilled in the art. For example, one skilled in the art will certainly be aware that these methods include *Agrobacterium*-mediated transformation by vacuum infiltration (Bechtold et al., 1993) or wound inoculation (Katavic et al., 1994), *Agrobacterium* Ti-plasmid-mediated transformation (e.g., hypocotyl (De Block et al., 1989) or cotyledonary petiole (Moloney et al, 1989) wound infection), particle bombardment/biolistic methods (Sanford et al., 1987; Nehra et al., 1994; Becker et al., 1994) or polyethylene glycol-assisted protoplast transformation (Rhodes et al., 1988; Shimamoto et al., 1989) methods.

As will also be apparent to persons skilled in the art, and as extensively reviewed elsewhere (Meyer, 1995; Datla et al., 1997), it is possible to utilize plant promoters to direct any intended up- or down-regulation of transgene expression using constitutive promoters (e.g., those based on CaMV35S), or by using promoters which can target gene expression to particular cells, tissues (e.g., napin promoter for expression of transgenes in developing seed cotyledons), organs (e.g., roots), to a particular developmental stage, or in response to a particular external stimulus (e.g., heat shock).

Particularly preferred plants for modification according to the present invention include borage (*Borago* spp.), Canola (*B. napus*, *B. rapa*, or *B. juncea*), castor (*Ricinus communis*), cocoa bean (*Theobroma cacao*), corn (*Zea mays*), cotton (*Gossypium* spp), Crambe spp., Cuphea spp., flax (*Linum* spp.), *Lesquerella* and *Limnanthes* spp., Linola, nasturtium (*Tropaeolum* spp.), Oenothera spp., olive (*Olea* spp.), palm (*Elaeis* spp.), peanut (*Arachis* spp.), high erucic rapeseed (*B. napus*) germplasm, safflower (*Carthamus* spp.), soybean (*Glycine* and *Soja* spp.), sunflower (*Helianthus* spp.), tobacco (*Nicotiana* spp.), *Vernonia* spp., wheat (*Triticum* spp.), barley (*Hordeum* spp.), rice (*Oryza* spp.), oat (*Avena* spp.) sorghum (*Sorghum* spp.), rye (*Secale* spp.) or other members of the Gramineae.

Methods of modulating PDHK content and composition in a plant is described in the incorporated U.S. Pat. No. 6,265,636 B1 to Randall et al. (see, e.g., columns 26 through 30 and 37 through 38).

The invention is further described by use of the following exemplary embodiments.

EXAMPLE 1

The PDHK gene was cloned from *Brassica napus* (cv. Quantum) (SEQ ID NO:1) by Reverse Transcription-Polymerase Chain Reaction (RT-PCR) amplification. Total RNA was extracted from young leaves (Wang and Vodkin, 1994) and cDNA produced by reverse transcription (Life Technologies, Inc., 2002, M-MLV Reverse Transcriptase page 16–25). Using this cDNA and several pairs of degenerate primers (SEQ ID NO:9 and SEQ ID NO:10) designed from conserved segments of known PDHK amino-acid sequences from *Arabidopsis* (CAA07447) and corn (AF038585), a fragment of about 1 kb was amplified by the Polymerase Chain Reaction (PCR). The fragment was cloned into the TOPO cloning vector (pCR TOPO 2.1, Invitrogen) and fully sequenced in both orientations (DNA lab, PBI/NRC). DNA sequence analysis revealed that this amplicon shared a high degree of homology with other known mtPDHK genes.

The missing termini of the gene were subsequently amplified using a 3' and 5' Rapid Amplification cDNA Ends (RACE) kit (Life Technologies, Inc., 2002, 3' RACE system and 5' RACE system pages 21–25). The full-length gene was then produced by PCR using Vent DNA polymerase (New England Biolabs) and gene specific primers (SEQ ID NO:11, SEQ ID NO:12, SEQ ID NO:13, SEQ ID NO:14, and SEQ ID NO:15) designed from the DNA sequence information provided by the RACE-generated fragments. These primers encompassed each end of the gene, i.e., the start and stop codons. At this stage, restriction sites were also added by PCR for subsequent anti-sense insertion of the PDHK gene into expression vectors such as pSE129A bearing the napin promoter (PBI/NRC) or pBBV-PHAS with the phaseolin promoter (courtesy of DowAgro Science). Orientation of the inserted gene was verified by restriction digestions and DNA sequencing.

DNA sequence analyses showed that the *B. napus* PDHK gene has an 1104 bp long open reading frame (386 AA). It was analyzed with respect to other PDHK sequences (GenBank) available and amino-acid comparison revealed 93% and 71% identity with *Arabidopsis* and corn sequences respectively. All DNA analyses (sequence alignments, primer design, etc.) were performed using the DNASTAR Lasergene™ software package.

EXAMPLE II

The same approach employed for cDNA cloning and sequence analysis of PDHK from *Brassica napus* as described in Example I was followed for the cloning and sequence analysis of the *B. rapa* PDHK gene (SEQ ID NO:2).

EXAMPLE III

The same approach employed for cDNA cloning and sequence analysis of PDHK from *Brassica napus* as described in Example I was followed for the cloning and sequence analysis of the *B. oleracea* PDHK gene (SEQ ID NO:3).

EXAMPLE IV

The same approach employed for cDNA cloning and sequence analysis of PDHK from *Brassica napus* as described in Example I was followed for the cloning and sequence analysis of the *B. carinata* PDHK gene (SEQ ID NO:4).

EXAMPLES V–VIII

The same approach employed for cDNA cloning and sequence analysis of PDHK from *Brassica napus* as described in Example I is followed for the cloning and sequence analysis of PDHK gene from *B. nigra, B. juncea, B. oleifera, B. balearica, B. cretica, B. elongata, B. tourneforii,* and *B. biennis.*

EXAMPLE IX

The oil content of a plant (e.g., borage (*Borago* spp.), Canola (*B. napus, B. rapa* or *B. juncea*), castor (*Ricinus communis*), cocoa bean (*Theobroma cacao*), corn (*Zea mays*), cotton (*Gossypium* spp), *Crambe* spp., *Cuphea* spp., flax (*Linum* spp.), *Lesquerella* and *Limnanthes* spp., Linola, nasturtium (*Tropaeolum* spp.), *Oenothera* spp., olive (*Olea* spp.), palm (*Elaeis* spp.), peanut (*Arachis* spp.), high erucic rapeseed (*B. napus*) germplasm, safflower (*Carthamus* spp.), soybean (*Glycine* and *Soja* spp.), sunflower (*Helianthus* spp.), tobacco (*Nicotiana* spp.), *Vernonia* spp., wheat (*Triticum* spp.), barley (*Hordeum* spp.), rice (*Oryza* spp.), oat (*Avena* spp.) sorghum (*Sorghum* spp.), rye (*Secale* spp.) or other members of the Gramineae)) is modified by first introducing an anti-sense nucleic acid construct into a plant transformation vector (e.g., one including a plant promoter) to produce a suitable plant transformation vector by means known to those of skill in the art (see, e.g., columns 26 to 30 of the incorporated U.S. Pat. No. 6,265,636 to Randall et al.) The anti-sense nucleic acid construct includes recombinant nucleic acid sequence encoding *Brassica* PDHK (e.g., the nucleic acid sequence of SEQ ID NO:1, SEQ ID NO:2, SEQ ID NO:3, or SEQ ID NO:4). The plant's genome is thus transformed (see, e.g., columns 33 through 37 of the incorporated U.S. Pat. No. 6,265,636) with the modified plant transformation vector. The plant seed is grown, and oil is extracted from the resulting plant seed.

EXAMPLE X

*Brassica napus* (Bn) PDHK in an anti-sense orientation modulates seed oil content and weight in *B. napus* strain Nex 710. The full length clone of the PDHK gene (SEQ ID NO:1) was inserted in an anti-sense orientation behind a phaseolin (PHAS) promoter (See, U.S. Pat. No. 5,504,200) in BBV-PHAS vector (Dow AgroSciences) and mobilized into *E. coli* (DH 5α) and *Agrobacterium* (GV3101 pMP90).

Two PmeI restriction (NEB) sites were added to the PDHK gene (SEQ ID NO:1) for cloning. The PDHK gene (SEQ ID NO:1) was inserted in anti-sense (a/s) orientation behind the PHAS promoter to form Bn PDHK-PHAS. The full length *B. napus* (Bn) PDHK gene (SEQ ID NO:1) was obtained by RT-PCR and RACE as previously described herein. Forward primer GTTTAAACATGGCGGTGAA-GAAGG (SEQ ID NO:16) and reverse primer GTT-TAAACTCATGGCAAAGGCTCC (SEQ ID NO:17) were designed to add a PmeI restriction site on each end of the PDHK gene. The full length Bn PDHK gene was amplified using PCR (with Vent polymerase, NEB) with primers (SEQ ID NO:16 and SEQ ID NO:17) that added the PmeI restriction sites. The amplified PCR product (amplicon) was run on a gel and cleaned from the agarose gel using a Qiagen kit. The cleaned PCR product was cloned into a TOPO cloning vector as previously described herein, transformed into *E. coli*, grown on media containing Ampicillin and the TOPO cloning vector including the PDHK gene was obtained using DNA preps (Qiagen).

The obtained TOPO cloning vector including the PDHK gene and the pBBV-PHAS-iaaH vector were digested with PmeI available from NEB. The digested pBBV-PHAS-iaaH vector was desphosphorylated, and the digested products were cleaned by running the products on a gel and purifying. The obtained PHDK gene and digested pBBV-PHAS-iaaH were blunt ligated with T4 ligase available from NEB. The ligated vector, including the PHDK gene, was electroporated into *E. coli* strain DH 12 S cells available from BRL in a ligation mixture, and the transformed cells were grown on media containing Spectinomycin. DNA preps (Qiagen) were performed on cells containing the vector to obtain Bn PDHK-PHAS. The orientation of the PDHK gene in the vector was checked by XhoI digestion since sense and anti-sense inserts of the PDHK gene result in different digestion patterns.

*Agrobacterium* (strain GV 3101, pMP90) was transformed by electroporation with an anti-sense (a/s) PDHK insert-containing DNA prep. The transformed *Agrobacterium* cells were grown on spectinomycin containing media, and DNA preps were collected and sequenced to check the size and orientation of the PHDK gene insert. The presence of the PHDK insert gene and its actual orientation were checked with several rounds of sequencing before plants were transformed.

*B. napus* line Nex 710 (Dow Agrosciences) was chosen as an elite line and used for transformation. About 7,000 *B. napus* explants (hypocotyls) were inoculated with the *Agrobacterium* containing the a/s PHAS: Bn PDHK construct. About 6,500 of the transformed explants formed a callus, and most of the explants formed shoots (transformed or not). After transfer of the explants in 3 different medias having gradually increasing levels of herbicide (L-PPT; 0.8–10 mg/l) for selection, 77 shoot explants were allowed to root in rooting media. Most of the explants formed roots and were PCR screened for the PDHK gene and the selection marker. 55 transformed plants were positive for PAT genes. More PCR reactions were preformed to check for the presence of the marker gene in the plant and the absence of a region of the vector that should not be inserted in the plant, i.e., outside the T-DNA borders, as negative controls.

Southern analyses using the PAT gene as a probe confirmed the transformation events, gave better estimates of the success of transformation (about 0.8%), and indicated the number of copies of the transgene that were inserted. 52 plants had one or several inserts, and 42 plants were retained for having 1 or 2 copies of the transgene.

Leaf painting with 3 mg/L Liberty was performed on $T_1$ plantlets and 10 resistant plants per line were selected. The first generation of transgenic lines was harvested and seeds were analyzed by gas chromatography (GC) for oil content. Several lines looked promising for having up to a 10% increase of seed oil. At this stage, the populations were still genetically segregating (the transgene insertion is hemizygous) and, therefore, the data on oil content represents an average value for each population of segregating genotype. 10 plants of each of the 42 lines that produced seeds were seeded in greenhouse for production of the $T_2$ generation.

42 lines were selected based on the number of inserted transgenes (1 or 2 copies of the transgene) for further generations. 10 plants per line were seeded, and the $T_2$ seeds were analyzed by GC for oil content. Several promising lines were identified and exhibited increased oil content. For instance, 16 lines had a 17% increase of oil content and 1 line had a 36% increase of oil content. Other promising cell lines had increased seed weight. For instance, 38 lines had a 16% increase in seed weight and 1 line had an 80% increase in seed weight. Other lines had increased total oil content on a per seed basis. 32 lines had a 27% increase in total oil content per seed and 1 line had a 78% increase of total oil per seed as compared to the control non-transformed wild type or the respective sibling null lines.

$T_3$ seeds (9 transgenic lines, 10 plants each, plus vector-only, nulls and wild type control lines) were harvested and analyzed for oil content, composition and average seed weight. The $T_3$ data are presented in FIGS. 1–4.

EXAMPLE XI

Utility of Bn PDHK (SEQ ID NO:1) in modulating flowering (generation) time. The Bn PDHK gene (SEQ ID NO:1) was inserted in an anti-sense orientation behind the Ubiquitin (UBQ) gene promoter (See, U.S. Pat. No. 6,054,574) in the pDAB4016M vector (Dow AgroSciences). The Bn PDHK gene was obtained by amplifying the full length Bn PDHK gene (obtained by RT-PCR, reverse transcription PCR, and RACE as previously described herein) with a forward primer CGTACGATGGCGGTGAAGAAGGCTA (SEQ ID NO:18) and a reverse primer GGTGACCTCATG-GCAAAGGCTCCT (SEQ ID NO:19) designed to add two restriction sites, BstE II and BsiW I, at each end of the Bn PDHK gene. The amplification was performed by PCR using Vent polymerase available from NEB. The PCR product was run on an agarose gel and cleaned using a Qiagen kit. The cleaned PCR product was cloned into a TOPO cloning vector as previously described herein and the TOPO cloning vector including the Bn PDHK gene was transformed into a cell. The transformed cell was grown on media including Ampicillin and the TOPO cloning vector including the Bn PDHK gene was obtained from the cells using DNA preps from Qiagen.

The TOPO preps and pDAB4016M vector (courtesy of Dow Agrosciences) were digested with BstE II and BsiW I restriction enzymes available from NEB. The digested pDAB4016M vector was dephosphorylated, and the digested products were cleaned by running on a gel and using a Qiagen kit. The digested pDAB4016M vector and the digested TOPO preps including the Bn PDHK gene were blunt ligated with T4 ligase available from NEB. *E. coli* strain DH 20B cells, available from BRL, were ligated with a ligation mixture including the ligated vector. The transformed cells were grown on media including Erythromycin and DNA preps (Qiagen) were performed to obtain the a/s Bn PDHK-DAB vector.

*Agrobacterium* strain GV 3101 pMP90 was transformed by electroporation with the a/s insert-containing DNA prep. The *Agrobacterium* cells were grown on media including Erythromycin, and DNA preps were performed to obtain the a/s insert-containing vector. The a/s insert-containing vectors were sequenced to check the size and orientation of the insert. The presence of the PDHK, the PAT marker gene and the Ubiquitin promoter was verified by PCR performed on DNA obtained from transformed *Agrobacterium* DNA.

9,000 explants (hypocotyls from the *B. napus* Nex 710 line) were transformed with *Agrobacterium* containing the a/s Bn PDHK-DAB vector (5,000 explants) or the pDAB vector as a control (4,000 explants). The transformed explants were selected on a LPPT-containing medium as known in the art, and the transformed explants were screened by PCR for the presence of the PDHK insert, the PAT gene and the UBQ promoter. 60 plants were analyzed by Southern blots (using a probe for the PAT marker gene) to check the number of transgenes that were inserted. The transformation rate was determined to be 0.9% and 37 plants with one or two copies of the insert were retained for further generations.

$T_1$ seeds were harvested and seeded in a greenhouse. The resulting plantlets were leaf-painted with Liberty herbicide to detect null-sib lines. 34 lines were retained (8–10 plants each) and 17 lines having a corresponding null-sib line were obtained as control, the rest of the lines had vector-only as a control.

Figure 5:
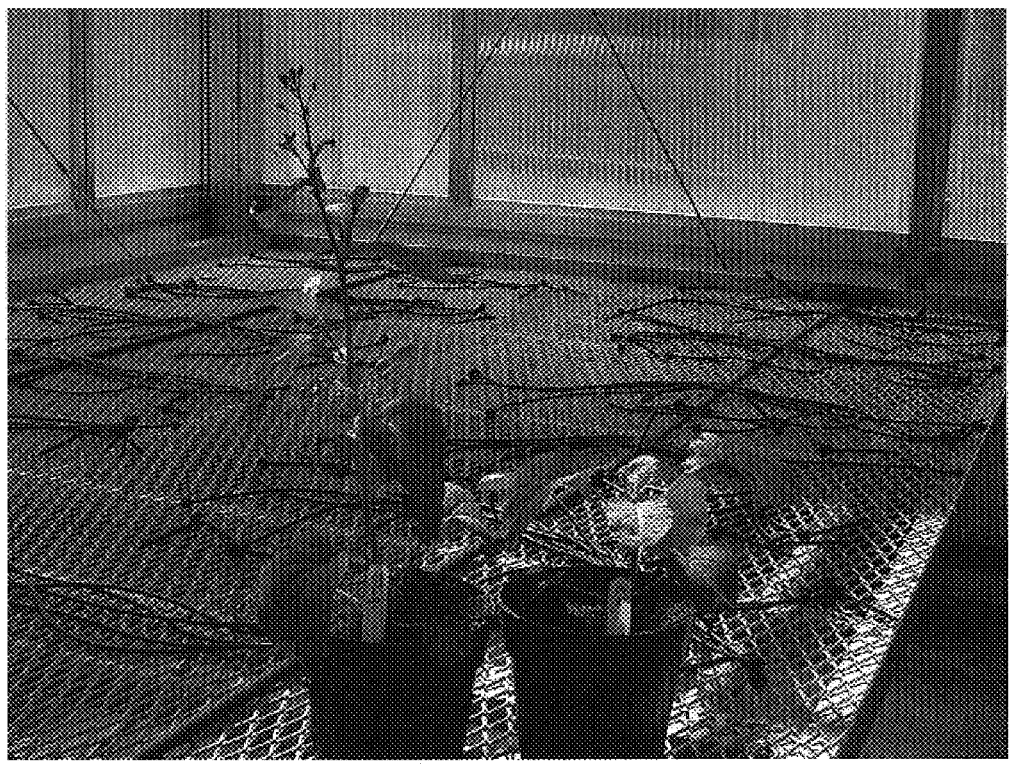
FIG. 5. Transgenic Nex710 UBP:a/sBnapusPDHK line 20-9 and its vector-only control on July 18th. The transgenic line (left hand side) is fully bolted and is ready to flower (floral buds are well-developed), while the control line (right hand side) bears several leaves only and did not flower until August 1st, 14 days later.
Figure 6:
FIG. 6. Transgenic Nex710 UBP:a/sBnapusPDHK lines 20-7 and 32-2 9 (right hand side (rhs)) and vector-only controls (left hand side (lhs)) on August 11th. The controls are in full bloom, while the transgenic lines are well into developing siliques, and have completed the flowering stage.

Most of the transformed *B. napus* Nex 710 plants displayed a significant early flowering phenotype in the $T_2$ generation as compared to the controls. FIG. 5 shows a transgenic plant with anti-sense PDHK flowering 2 weeks earlier than the control. Thus, the transformed plant exhibits a 15% shorter cycle when assuming an average cycle of 100 days. A demonstration of early flowering by down-regulating PDHK gene in *B. napus* Nex 710, a double haploid (DH) line which is known for uniform maturity, demonstrates the utility of manipulating the expression of the PDHK gene in eliciting early flowering.

Although described with the use of particular exemplary examples and embodiments, the scope of the invention is to be determined by the appended claims.

REFERENCES

Bechtold, N., Ellis, J. and Pelletier, G. (1993) In planta *Agrobacterium*-mediated gene transfer by infiltration of adult *Arabidopsis thaliana* plants. *C.R. Acad. Sci. Ser. III Sci. Vie*, 316: 1194–1199.

Becker, D., Brettschneider, R. and Lörz, H. (1994) Fertile transgenic wheat from microprojectile bombardment of scutellar tissue. *Plant J.* 5: 299–307.

Datla, R., Anderson, J. W. and Selvaraj, G. (1997) Plant promoters for transgene expression. *Biotechnology Annual Review* 3: 269–296.

De Block, M., De Brouwer, D. and Tenning P. (1989) Transformation of *Brassica napus* and *Brassica oleracea* using *Agrobacterium tumefaciens* and the expression of the bar and neo genes in the transgenic plants. *Plant Physiol.* 91: 694–701.

Jorgensen, R. A. and Napoli, C. A. (1994) Genetic engineering of novel plant phenotypes. U.S. Pat. No. 5,283,184.

Katavic, V., Haughn, G. W., Reed, D., Martin, M. and Kunst, L. (1994) In planta transformation of *Arabidopsis thaliana*. *Mol. Gen. Genet.* 245: 363–370.

Kishore G. M. and Somerville, C. R. (1993) Genetic engineering of commercially useful biosynthetic pathways in transgenic plants. *Current Opinion in Biotechnology.* 4: 152–158.

MacKenzie, S. L. and Jain, R. K. (1997) Improvement of oils crops via biotechnology. *Recent Res. Dev. In Oil Chem.* 1: 149–158.

Meyer, P. (1995) Understanding and controlling transgene expression. *Trends in Biotechnology,* 13: 332–337.

Moloney, M. M., Walker, J. M. and Sharma, K. K. (1989) High efficiency transformation of *Brassica napus* using *Agrobacterium* vectors. *Plant Cell Rep.* 8: 238–242.

Nehra, N. S., Chibbar, R. N., Leung, N., Caswell, K., Mallard, C., Steinhauer, L. Baga, M. and Kartha K. K. (1994) Self-fertile transgenic wheat plants regenerated from isolated scutellar tissues following microprojectile bombardment with two distinct gene constructs. *Plant J.* 5: 285–297.

Padgette, S. R., Gruys, K. J., Mitsky, T. A., Tran, M., Taylor, N. B., Slater, S. C. and Kishore, G. M. (1997) Strategies for production of polyhydroxyalkanoate polymers in plants. *Plant Physiol.* Suppl., 114: 3 (abstract 10003).

Potrykus, I. (1991) Gene transfer to plants: Assessment of published approaches and results. *Annu. Rev. Plant Physiol. Plant Mol. Biol.* 42: 205–225.

Rhodes, C. A., Pierce, D. A., Mettler, I. J., Mascarenhas, D. and Detmer, J. J. (1988) Genetically transformed maize plants from protoplasts. *Science* 240: 204–207.

Sanford, J. C., Klein, T. M., Wolf, E. D. and Allen, N. (1987) Delivery of substances into cells and tissues using a particle bombardment process. *J. Part. Sci. Technol.* 5: 27–37.

Shimamoto, K., Terada, R., Izawa, T. and Fujimoto, H. (1989) Fertile transgenic rice plants regenerated from transformed protoplasts. *Nature* 338: 274–276.

Somerville, C. R. (1993) Future prospects for genetic modification of the composition of edible oils from higher plants. *Am. J. Clin. Nutr.* 58 (2 Suppl.): 270S–275S.

Songstad, D. D., Somers, D. A. and Griesbach, R. J. (1995) Advances in alternative DNA delivery techniques. *Plant Cell, Tissue and Organ Culture* 40: 1–15.

Vasil, I. K. (1994) Molecular improvement of cereals. *Plant Mol. Biol.* 25: 925–937.

Walden, R. and Wingender, R. (1995) Gene-transfer and plant regeneration techniques. *Trends in Biotechnology* 13: 324–331.

Wang, C-S and Vodkin, L. O. (1994) Extraction of RNA from tissues containing high levels of procyanidins that bind RNA. *Plant Molecular Biology Reporter* 12: 132–145.

What is claimed is:

1. A transgenic plant, comprising:
   an isolated nucleic acid sequence incorporated into the plant's genome having a sequence selected from the group of sequences consisting of SEQ ID NO:1, SEQ ID NO:2, SEQ ID NO:3 and SEQ ID NO:4; and
   a promoter operatively linked to the nucleic acid sequence.

2. The transgenic plant of claim 1, wherein the plant is selected from the group consisting of borage, Canola, castor, cocoa bean, cotton, *Crambe* spp., *Cuphea* spp., flax, *Lesquerella* and *Limnanthes* spp., Linola, nasturtium, *Oenothera* spp., olive, palm, peanut, rapeseed, safflower, soybean, sunflower, tobacco, *Vernonia* spp and members of the Gramineae.

3. The transgenic plant of claim 2 wherein the member of the Gramineae is selected from the group consisting of corn, wheat, barley, rice, oat, sorghum and rye.

4. The transgenic plant of claim 2, wherein the plant is Canola.

5. The transgenic plant of claim 1, wherein the nucleic acid sequence further comprises a nucleic acid sequence encoding a pyruvate dehydrogenase kinase oriented in an anti-sense direction.

6. The transgenic plant of claim 1, wherein the promoter is an ubiquitin gene promoter.

7. The transgenic plant of claim 1, wherein the promoter is a phaseolin promoter.

8. A process for modulating mitochondrially generated acetyl-CoA and/or respiration rate in a transgenic plant, the process comprising:
   cloning a gene encoding a *Brassica* pyruvate dehydrogenase kinase protein into a vector, wherein the gene comprises a sequence selected from the group consisting of SEQ ID NO:1, SEQ ID NO:2, SEQ ID NO:3 and SEQ ID NO:4;
   positioning the gene in an anti-sense orientation within the vector; and
   transforming a plant with the vector to produce the transgenic plant.

9. The process according to claim 8, further comprising: linking a promoter to the gene.

10. The process according to claim 9, wherein the promoter is an ubiquitin gene promoter or a phaseolin promoter.

11. The process according to claim 8, wherein the plant is selected from the group consisting of borage, Canola, castor, cocoa bean, cotton, *Crambe* spp., *Cuphea* spp., flax, *Lesquerella* and *Limnanthes* spp., Linola, nasturtium, *Oenothera* spp., olive, palm, peanut, rapeseed, safflower, soybean, sunflower, tobacco, *Vernonia* spp and members of the Gramineae.

12. The process of claim 11 wherein the member of the Gramineae is selected from the group consisting of corn, wheat, barley, rice, oat, sorghum and rye.

13. The process according to claim 11, wherein the plant is Canola.

14. A transgenic plant produced by the process according to claim 8.

15. A process for modulating mitochondrially generated acetyl-COA and/or respiration rate in a transgenic plant, the process comprising:
   cloning a gene encoding a *Brassica* pyruvate dehydrogenase kinase protein into a vector, wherein the gene comprises a sequence selected from the group of sequences consisting of SEQ ID NO:1, SEQ ID NO:2, SEQ ID NO:3 and SEQ ID NO:4;
   transforming the vector into a plant to produce a transgenic plant; and
   selecting a transgenic plant having reduced production of the *Brassica* pyruvate dehydrogenase kinase protein in the transgenic plant.

16. The process according to claim 15, wherein the plant is selected from the group consisting of borage, Canola, castor, cocoa bean, cotton, *Crambe* spp., *Cuphea* spp., flax, *Lesquerella* and *Limnanthes* spp., Linola, nasturtium, *Oenothera* spp., olive, palm, peanut, rapeseed, safflower, soybean, sunflower, tobacco, *Vernonia* spp and members of the Gramineae.

17. The process of claim 16 wherein the member of the Gramineae is selected from the group consisting of corn, wheat, barley, rice, oat, sorghum and rye.

18. The process according to claim 16, wherein the plant is Canola.

19. The process according to claim 15, wherein the gene encoding the *Brassica* pyruvate dehydrogenase kinase protein is in an anti-sense orientation in the vector.

20. A transgenic plant produced by the process according to claim 15.

21. A combination of isolated DNA fragments comprising SEQ ID NO:1, SEQ ID NO:2, SEQ ID NO:3 and SEQ ID NO:4.

22. A transgenic plant, comprising:
   an isolated nucleic acid transformed into the plant's genome having the sequence of SEQ ID NO:1; and
   a promoter operatively linked to the isolated nucleic acid transformed into the plant's genome.

* * * * *